United States Patent [19]
McGuire

[11] Patent Number: 5,203,699
[45] Date of Patent: Apr. 20, 1993

[54] SUCTION ADAPTER FOR USE WITH ABSORBENT ROLL HOLDER

[76] Inventor: Jimmie L. McGuire, 2938 Ramble Rd. West, Bloomington, Ind. 47408

[21] Appl. No.: 733,441

[22] Filed: Jul. 22, 1991

[51] Int. Cl.⁵ .................... A61C 17/06; A61C 17/14
[52] U.S. Cl. .................................... 433/93; 433/91
[58] Field of Search ................ 433/91, 93, 94, 95, 433/96

[56] References Cited

U.S. PATENT DOCUMENTS

| | | | |
|---|---|---|---|
| 950,109 | 2/1910 | Levkowicz . | |
| 1,401,646 | 12/1921 | Ronn . | |
| 1,742,080 | 12/1929 | Jones | 433/93 |
| 2,180,249 | 11/1939 | Lempert | 32/33 |
| 2,507,938 | 5/1950 | Smith | 433/94 |
| 2,587,008 | 2/1952 | Stadelmann | 32/33 |
| 2,625,739 | 1/1953 | Garmers | 32/35 |
| 2,637,106 | 5/1953 | Otis | 32/33 |
| 2,644,234 | 7/1953 | Scott | 32/33 |
| 2,791,030 | 5/1957 | Tofflemire | 32/63 |
| 2,823,455 | 2/1958 | Sprague | 433/93 |
| 2,844,873 | 7/1958 | Bober | 433/94 |
| 2,859,519 | 11/1958 | Cohn | 433/93 |
| 2,914,852 | 12/1959 | Fridge, Sr. | 32/35 |
| 2,950,533 | 8/1960 | Sommerstein | 32/33 |
| 3,049,806 | 8/1962 | Cofresi | 32/33 |
| 3,091,859 | 6/1963 | Baughan | 32/33 |
| 3,101,543 | 8/1963 | Baughan | 32/33 |
| 3,148,449 | 9/1964 | Van Lanigan | 32/33 |
| 3,396,468 | 8/1968 | Dayhoff | 32/33 |
| 3,426,430 | 2/1969 | Newman | 433/96 |
| 3,520,300 | 7/1970 | Flower, Jr. | 128/276 |
| 3,924,333 | 12/1975 | Erickson | 433/93 |
| 4,053,984 | 10/1977 | Moss | 32/33 |
| 4,068,664 | 1/1978 | Sharp et al. | 128/276 |
| 4,205,677 | 6/1980 | Engstrom | 433/95 X |
| 4,215,984 | 8/1980 | Reichley | 433/93 |
| 4,233,025 | 11/1980 | Larson et al. | 433/136 |
| 4,240,789 | 12/1980 | Rosenthaler | 433/136 |
| 4,260,378 | 4/1981 | O'Neil | 433/93 |

FOREIGN PATENT DOCUMENTS

| | | | |
|---|---|---|---|
| 459486 | 5/1928 | Fed. Rep. of Germany | 433/94 |
| 761736 | 9/1935 | France | 433/94 |
| 242045 | 4/1946 | Switzerland | 32/33 |

*Primary Examiner*—Gene Mancene
*Assistant Examiner*—Nicholas D. Lucchesi
*Attorney, Agent, or Firm*—Woodard, Emhardt, Naughton Moriarty & McNett

[57] ABSTRACT

A suction adapter is provided for use with an absorbent roll holder, and particularly for providing suction to hollow absorbent rolls supported by the roll holder within the mouth of a patient. In one embodiment, the suction adapter includes a body having an outwardly opening slot formed therein for removable engagement with the frame of the roll holder, which in one specific embodiment is a Garmers type device. The body further includes a pair of passages formed therethrough, one end of the passages opening in suction orifices at one face of the body and the other end of the passages opening in tube attachment bores at another face of the body. The suction orifices are arranged for fluid communication with a vacuum source by application of the suction hose to the one face of the body surrounding the suction orifices. The tube attachment bores are sized to receive one end of suction tubes, which tubes are adapted to engage the central lumen of the hollow absorbent rolls supported by the Garmers device. In another embodiment, the suction tubes are combined in a suction adaptor tube. A slide collar is disposed around the suction tubes to adjust the configuration of the tubes within the patient's mouth.

13 Claims, 3 Drawing Sheets

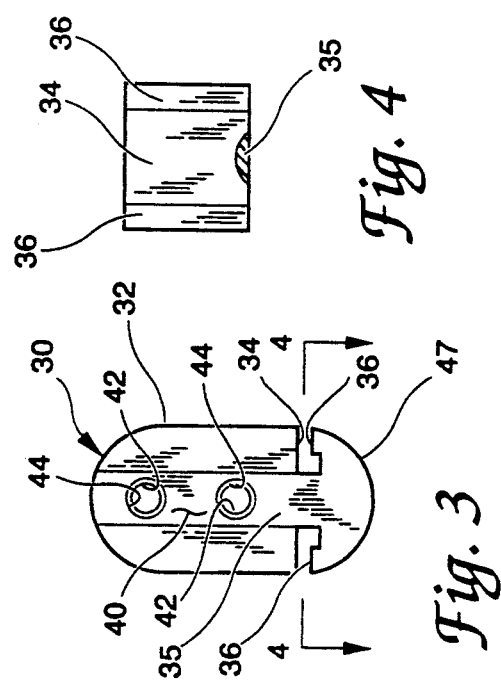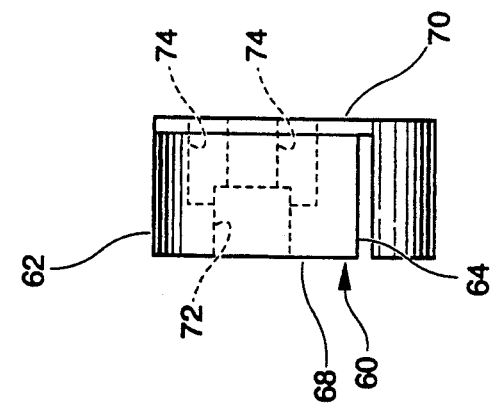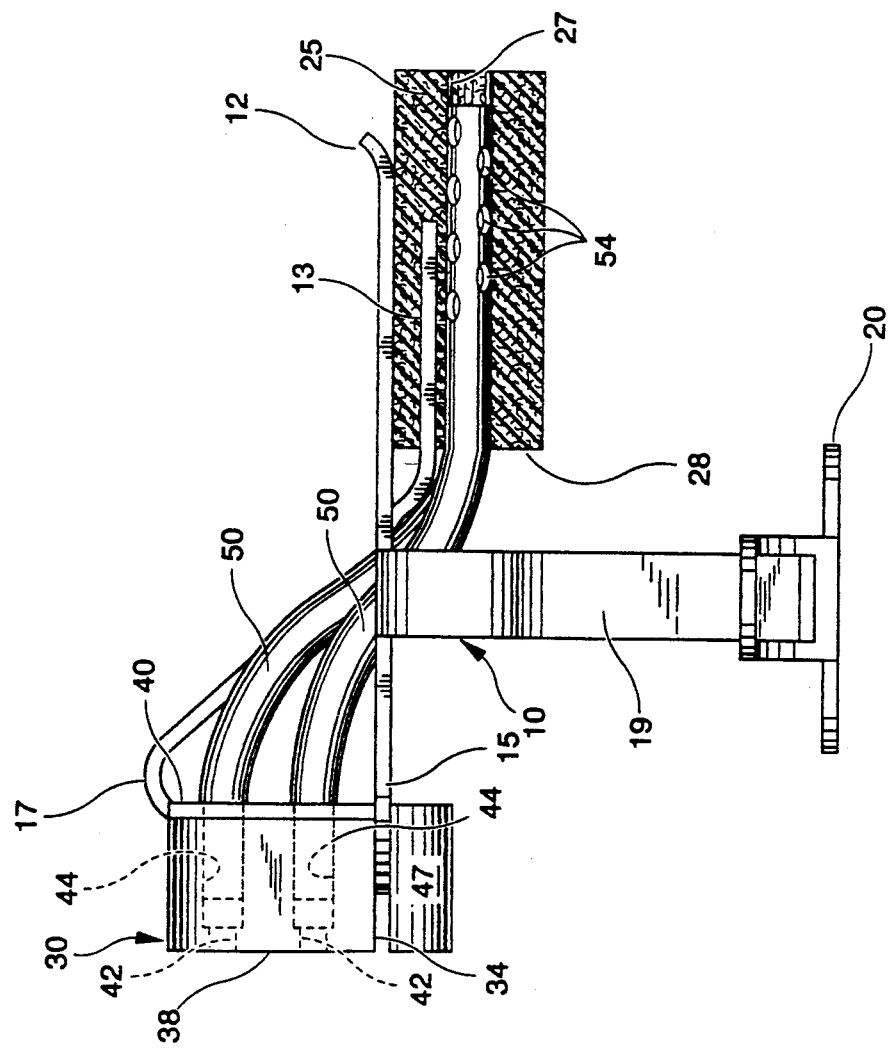

SUCTION ADAPTER FOR USE WITH ABSORBENT ROLL HOLDER

BACKGROUND OF THE INVENTION

This invention relates generally to dental instruments for removing or ejecting saliva from the mouth of a patient during a dental procedure. More particularly, the invention relates to a dental instrument having structure for supporting absorbent rolls and for providing an interface between the supported rolls and a vacuum source when the absorbent rolls are in their operative positions within the patient's mouth.

In the field of dentistry, it is well known that mucous, saliva and other fluids can accumulate within the mouth of a patient during various dental procedures. Fluid accumulation in the patient's mouth is particularly nettlesome during procedures performed on the lower teeth of the patient since the fluid has a tendency to invade the work area. Thus, dentists or dental assistants have used a variety of methods to absorb and/or remove fluids from the patient's mouth during the course of the dental procedure.

In one of the more common methods, a device known in the trade as a Garmers cotton roll holder is used to retain a pair of cotton rolls in engagement about the alveolar ridge. The supported cotton rolls absorb the saliva and fluids, keeping the work area clear around the patient's teeth. The Garmers device is described in U.S. Pat. No. 2,625,739.

The traditional Garmers device simply provides means for supporting absorbent rolls within the patient's mouth. However, the device does not provide means for ejecting or removing the saliva. Thus, it is frequently necessary to replace the cotton rolls several times during a given dental procedure as the rolls become soaked. Many instruments have been developed for ejecting or removing saliva, such as the device described in the patent to Scott, U.S. Pat. No. 2,644,234. In this instrument, a pair of absorbent cotton rolls are engaged over a perforated stainless steel tube which is then connected to a source of continuous suction. Other types of saliva ejectors are known in which the absorbent cotton roll is replaced by perforated tubes. The patents to Van Lanigan, U.S. Pat. No. 3,148,449, and Baughan, U.S. Pat. No. 3,091,859, are examples of this type of instrument.

One difficulty that has been encountered by these saliva ejector instruments is the inability to provide for intermittent suction, rather than continuous suction. Devices such as the Van Lanigan and Baughan instruments above do not provide means for intermittent engagement to a suction source during a dental procedure. Intermittent suction is often preferred in modern practice where the patient'sits upright during the procedure.

Another drawback of many of the prior devices is that only a small portion of the suction components are replaceable or disposable. For instance, in the Baughan device, perforated rubber tips are mounted on tubular structure. While the rubber tips are disposable, the tubular mounting structure is intended to be reused. Reuse requires significant effort to clean and sterilize the support structure.

A drawback common with most prior continuous suction devices is that the suction tube infringes upon the work area and requires constant repositioning by the dental assistant. This repositioning can become cumbersome and prevents the oral surgeon or dentist from working without an assistant.

There is therefore a need recognized in the field for a device which is completely disposable and which does not require a fixed structure which must be cleaned and sterilized between procedures. There is also a need for such a device that is inexpensive, thereby justifying its ready disposability. It is further desirable that the device include means for providing intermittent suction to the work area to eject saliva and fluids, without requiring constant attention of a dental assistant.

SUMMARY OF THE INVENTION

In view of the drawbacks of prior saliva ejectors and roll holders, the present invention contemplates means for adapting an absorbent roll holder type dental instrument for engagement to a suction source of saliva ejector.

In one aspect of the invention, a number of tubes are provided for insertion into the central bore of a corresponding absorbent roll, which roll is supported by the dental instrument for operative positioning within the patient's mouth. The tubes include a number of perforations at the opposite end which communicate with the central lumen of the tube. Suction provided through the central lumen of the tubes draws saliva and other fluids from the patient's mouth, through the absorbent rolls and into the suction tubes to keep the work area dry.

In another aspect of one embodiment of the invention, an adapter assembly is provided which includes a body having means in the body for engaging the dental instrument so that the body is supported by the instrument. The body further includes a number of passages extending therethrough which open at one face in a number of suction orifices and at another face in a number of tube attachment bores The tube attachment bores are provided for sealing engagement with one end of each tube. The suction orifices are arranged on the body for intermittent application of a suction hose to draw a vacuum through the body passages and ultimately through the suction tubes connected at the tube attachment bores.

In another embodiment of the invention, a suction tube arrangement includes a pair of perforated suction tubes that are engaged within the central bore of corresponding absorbent rolls. The rolls are supported by a dental instrument, such as a roll holder, within the patient's mouth. The external ends of the suction tubes are engaged within the bore of a larger suction adaptor tube. A mating tube is engaged at the opposite end of the suction adaptor tube to facilitate quick intermittent attachment to the suction hose of a suction source. A slide collar is engaged about the two suction tubes between the suction adaptor tube and the dental instrument. The slide collar can be moved over the two tubes to vary the configuration of the tubes within the patient's mouth.

It is one object of the invention to provide means for engagement of suction tubes with a dental instrument, such as an absorbent roll holder, which tubes can be engaged to a suction source. Another object is to provide such means that is readily replaceable and disposable.

Yet another object is in the provision of an adapter or suction tube arrangement that can be configured for use with a variety of dental instruments. A further object is for an adapter or suction tube arrangement that can be used with the dental instrument without interfering with the work area or causing trauma to the patient.

Other objects of the invention, as well as its many benefits, will become apparent upon consideration of the following written description and accompanying figures.

BRIEF DESCRIPTION OF THE DRAWINGS

FIG. 2 is a side elevational view of the one embodiment shown in FIG. 1.

FIG. 3 is an elevational view of one face of the suction adapter assembly shown in FIG. 1.

FIG. 4 is a top cross-sectional view of the suction adapter assembly shown in FIG. 3 taken along the line 4—4 as viewed in the direction of the arrows.

FIG. 5 is a side elevational view of an alternative embodiment of the suction adapter assembly of the present invention.

DESCRIPTION OF THE PREFERRED EMBODIMENT

Figure 1:
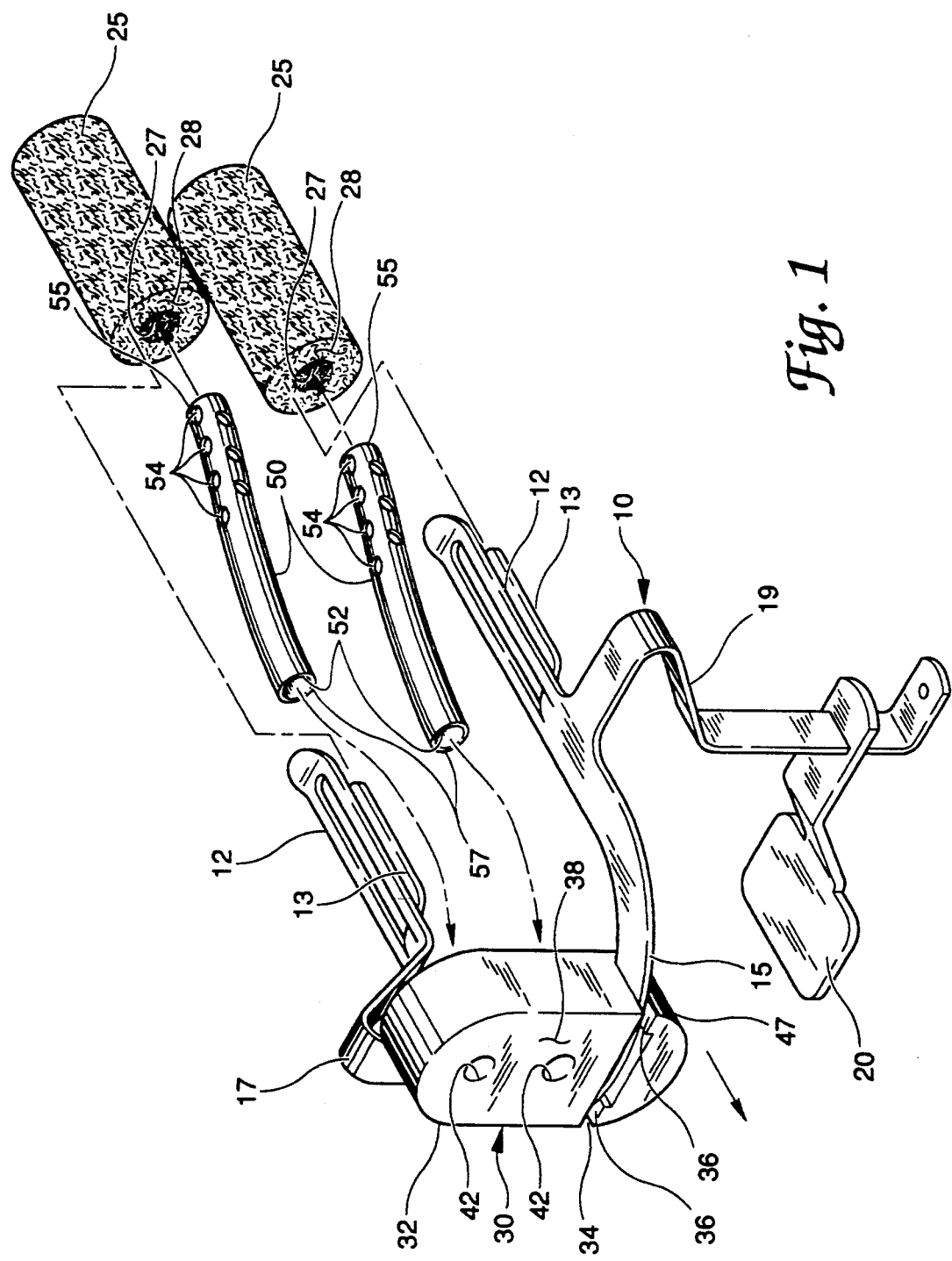
FIG. 1 is a perspective view of one embodiment of a suction adapter assembly of the present invention, shown in a partial exploded view, as engaged about a Garmers type dental instrument.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention concerns a suction adapter assembly which can be readily mounted on a dental instrument, such as the Garmers cotton roll holder. Thus, in FIG. 1, a Garmers device 10 is depicted which includes a pair of roll-retaining members 12. Each of the roll-retaining members includes a roll piercing prong 13 which is used to pierce a cotton roll in the manner described in the patent to Garmers, U.S. Pat. No. 2,625,739. The device 10 further includes a frame for supporting the roll-retaining members within the mouth of a patient. The frame includes an interconnection bar 15 which connects the two roll-retaining members 12. One of the retaining members 12 is connected to the bar 15 by way of a tooth bridge 17 which is configured to pass over the front teeth of the patient when the device is in its operative position within the patient's mouth. The frame of the device 10 further includes a clamp mounting arm 19 which connects the bar 15 to a chin clamp 20 which holds the device in its operative position.

It is understood that the device 10 thus far described is substantially identical to the Garmers device shown and described in the '739 patent. For purposes of illustration, the description of this device in U.S. Pat. No. 2,625,739 patent is incorporated herein by reference. However, it is understood that only a preferred embodiment of the present invention is described herein, which preferred embodiment is adapted for use with a Garmers type dental instrument.

Referring again to FIG. 1, a pair of absorbent rolls 25 are provided which are engaged by the roll piercing prongs 13 of the Garmers device 10. In a modification from the absorbent roll depicted in the Garmers '739 patent, each absorbent roll 25 includes a central bore 27. In this respect, the absorbent roll 25 is similar to the absorbent roll shown and described in the patent to Scott, U.S. Pat. No. 2,644,234. The roll 25 is adapted to be engaged on the roll-retaining members 12 by pushing the prongs 13 through the end face 28 of the roll 25. It is understood that the absorbent roll 25 can be formed of any absorbent material. For instance, the roll can be formed of cotton or of an absorbent polyurethane foam material, such as described in the patent to Larson et al. U.S. Pat. No. 4,233,025. The primary requirement for the configuration of the absorbent rolls 25 is that each includes a central bore 27 and sufficient area at the end face 28 to be impaled upon one of the piercing prongs 13 of the roll-retaining members 12.

The elements thus far described can be used in a typical manner for a Garmers type device in which the absorbent rolls 25 are supported by the roll-retaining members 12 and simply provide absorption within the patient's mouth. In order to enhance the performance of the absorbent rolls 25, means are provided for applying suction at the work area within the patient's mouth. More particularly, means are provided for applying suction through the absorbent rolls 25, thereby increasing the length of time that a single absorbent roll 25 may be used and increasing the capability for removing saliva and other fluids from the work area. Moreover, the application of fluid suction at the work area can keep the absorbent rolls 25 substantially dry and the work area substantially clear of fluids during a dental procedure.

In one embodiment of the invention, a suction adapter assembly 30 is provided which includes a body 32. The body 32 is generally oblong in shape and includes a mounting slot 34 extending from one face of the body 32. The mounting slot 34 terminates at its closed end in a mounting stem 35, as shown more clearly at FIGS. 3 and 4. The mounting stem 35 as depicted in FIG. 4 is curved to conform to the curvature of the interconnection bar 15 of the device 10. As shown in FIGS. 1 and 3, the body 32 further includes a pressure ridge 36 at the lower portion of the mounting slot 34 which engages the interconnection bar 15. As is apparent from FIGS. 1 and 2, the body 32 is supported by the interconnection bar 15 of the device 10 when the bar 15 is disposed within the mounting slot 34.

The body 32 includes a suction face 38 and an opposite tube attachment face 40 (see FIG. 2). A pair of parallel passageways are formed within the body 32 which open at the suction face 38 in a suction orifice 42 and at the tube attachment face 40 in a tube bore 44. As shown more clearly in FIGS. 2 and 3, the suction orifice 42 is smaller in effective diameter than the tube bore 44.

Another element of the suction adapter 30 are the suction tubes 50. Each of the suction tubes 50 includes a central lumen 52 which is in fluid communication with a number of apertures 54 adjacent one end 55 of the suction tube 50. The opposite attachment end 57 of the tube 50 is engaged within one of the tube bores 44 in the body 32. In the preferred embodiment, the outer diameter of the suction tubes 50 is equal to or slightly larger than the diameter of the tube bores 44 to ensure a press-fit engagement between the suction tubes 50 and the body 32. The fit must be sufficiently tight to ensure a seal as a vacuum is drawn through the suction tubes 50 and tube bores 44.

It should also be clear that the central bore 27 through each of the absorbent rolls 25 should also be equal to or slightly smaller in diameter than the outer diameter of the suction tube 50 to ensure a tight fit between the suction tube 50 and the absorbent roll 25. Although removable press-fit engagements have been described as the preferred embodiment, it is also within the scope of the invention to permanently fix each of the tubes at their respective ends to the body 32 and/or to the absorbent rolls 25, depending upon which, if any, of the components are intended for reuse. Disposable components can be permanently joined, while reusable components must be removable from the disposable elements.

The tubes 50 must be sufficiently long to provide adequate engagement with the bores 40 and the rolls 25 and to resist disengagement therefrom when exposed to operative conditions. On the other hand, tubes that are too long can tend to push the rolls 25 off the prongs 13, or may bend and pinch between the body 32 and the rolls 25.

It is understood that the geometry of the suction adapter assembly 30 and particularly the body 32 can be adapted to accommodate various geometries of dental instruments. In the preferred embodiment, the suction orifices 42 within the suction face 38 of the body 32 are closely located so that a single suction tube connected to a vacuum source can be engaged over both orifices. Separate orifices 42 can be provided as shown in FIG. 1 so that suction can be independently applied to one or the other of the suction tubes 50 and absorbent rolls 25 on either the lingual or buccal side of the alveolar ridge.

Alternatively, a single suction orifice may be provided which communicates internally with separate tube bores. Referring to FIG. 5, an alternative embodiment of the invention is depicted in which an adapter assembly 60 includes a body 62 having a slot 64 for engaging the dental instrument 10. The body 62 further includes a suction face 68 and attachment face 70 with a passage communicating therethrough. In a deviation form the prior embodiment, the passage through the body 62 includes a single suction orifice 72 which communicates with both tube attachment bores 74. Other alternative configurations that provide some means for sealingly engaging a suction tube at the attachment face of the body fall within the scope of the invention. For instance, a nipple may project from the attachment face 40 of the body 32 (FIGS. 1-3), whereby the central lumen 57 of the suction tube is pressed onto the nipple.

Referring again to FIG. 1, another aspect of the geometry of the suction adapter assembly body 32 is the configuration of the mounting slot 34. While the slot 34 in the preferred embodiment is narrow to accept the interconnection bar 15 of a Garmers device 10, other slot configurations are contemplated. For instance, the device may be of a wire construction, such as the cotton roll holder shown and described in the patent to Fridge, Sr., U.S. No. Pat. 2,914,852. The dental instrument may be of tubular construction or may have a different curvature than that shown in FIG. 1. Modifications in the body 32 and slot 34 to accommodate various geometries of dental instruments and roll holders are within the ordinary skill in the field. It is important, however, that the body 32 be adequately supported on the frame of the dental instrument and that the overall dimensions of the body 32 not be so great as to obstruct the work area within the patient's mouth or cause discomfort for the patient as the device contacts the patient's gum or lip.

In the preferred embodiment, the body 32 is formed from a molded polyurethane plastic. Other soft hygienic materials may be used to form the body. It is important though that the material of the body 32 be sufficiently resilient and soft to be as atraumatic as possible to the patient. It is also important that the body have sufficient resilience to remain in position on the interconnection bar 15 of the Garmers device 10.

The attachment face 40 and lower surface 47 of the body 32 will contact the patient's lip and chin when the device 10 is in its operative position. Thus, the oblong shape of the body 32 in the preferred embodiment eliminates sharp edges that may be irritating to the patient. Other modifications in the outer geometry of the body 32 may be made to conform to facial and oral features of the patient.

The suction adapter assembly 30 of the present invention can be readily engaged on a known dental instrument, such as the Garmers device 10. As depicted by the arrows in FIG. 1, the body 32 is advanced onto the interconnection bar 15 of the device 10 so that the bar 15 resides snugly within the slot 34. The end 57 of the tubes 50 can be inserted into a respective one of the tube attachment bores 44. The absorbent rolls 25 are then impaled upon the prongs 13 and the ends 55 of the tubes 50 inserted into the central bores 27 of a respective roll 25. Alternatively, the entire assembly 30 may be constructed prior to engagement on the device 10.

After use, the assembly 30 can be readily removed from the device 10 by pulling the rolls 25 from the prongs 13 and removing the body 32 from the interconnection bar 15. The disposable components, which include at least the soaked rolls 25, can be disposed of. Preferably, each of the tubes 50 are disposable. The body 32 can be cleaned and sterilized for reuse, but may also be discarded after one or several uses.

In addition to the disposability of the suction adapter 30, another advantage of the invention is in the provision of the suction orifices 42 at the suction face 38 of the body 32. The flat suction face 38 provides means for ready intermittent engagement of a conventional suction hose connected to a vacuum source by simply touching the end of the hose to the face 38 surrounding the orifices 42.

Figure 6:
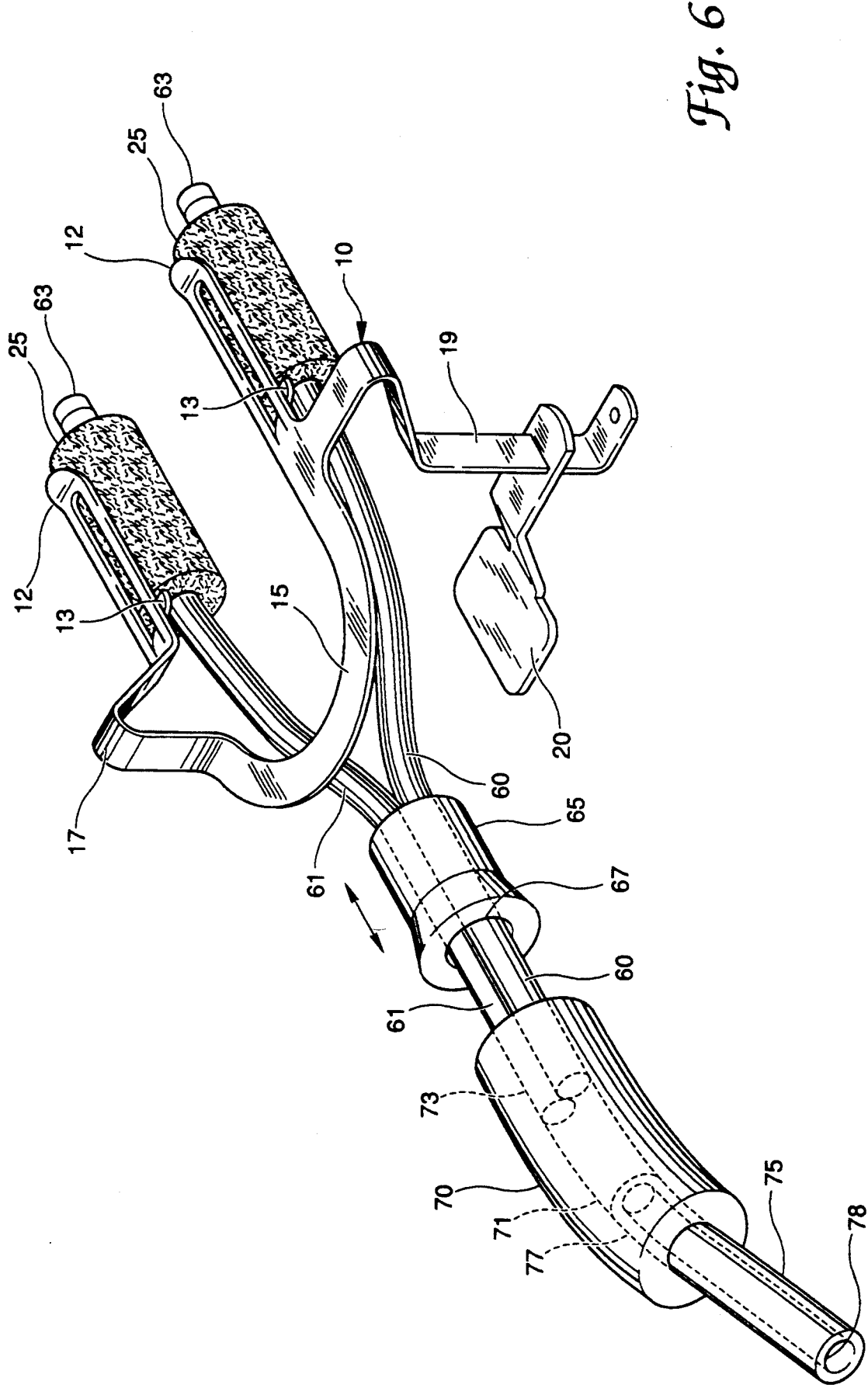
FIG. 6 is a perspective view of one embodiment of a suction tube arrangement of the present invention as engaged about a Garmers type dental instrument.

A further embodiment of the present invention is shown in FIG. 6 in which a suction tube arrangement provides the means for providing suction to absorbent rolls supported by a Garmers type dental instrument 10. A pair of absorbent rolls 25 are impaled on the prongs 13 of the Garmers device in the manner previously described. The suction tube arrangement includes a buccal side suction tube 60 and a lingual side suction tube 61 which extend through the respective central bores of the absorbent rolls. The suction tubes 60 and 61 are perforated in the same manner as the tubes 50 of the previous embodiment and are situated within the absorbent rolls so that the perforations are disposed within the rolls to extract fluid from the rolls. In one aspect of the present embodiment, the ends of the tubes 60 and 61, shown projecting beyond the absorbent rolls in FIG. 6, are capped by a restrictor plug 63. The restrictor plug 63 can be configured to completely close the end of the suction tubes 60 and 61, or the plug 63 can include an orifice therethrough (not shown) so that some fluid can be drawn through the plug.

The tubes 60 and 61 are long enough to extend a substantial length outside the patient's mouth. The buccal tube 60 passes under the interconnection bar 15 of the Garmers device so that the tube 60 is typically held between the patient's lower lip and the bar 15 when the Garmers device is in its operative position. The lingual tube 61 passes over the interconnection bar 15 in the operative position. The length of the tubes 60 and 61 is sufficient to permit adjustment of the position of the tubes within the patient's mouth. The tubes pass through the bore 67 of a slide collar 65, which collar can be adjusted in the direction of the arrows in FIG. 6. The slide collar 65 provides means for drawing the tubes into immediate adjacent relationship at adjustable locations along the lengths of the tubes, which then controls the amount of "slack" of the tubes within the patient's mouth. Adjustment of the slide collar 65 controls the configuration of the tubes 60 and 61 to best accommodate the patient's mouth.

The suction tube arrangement of the present embodiment also comprises a larger suction adaptor tube 70 which includes a central suction bore 71. The external ends of the buccal and lingual tubes 60 and 61 are engaged within the bore 71 at the end 73 of the adaptor tube 70. It is apparent that the bore 71 of the adaptor tube 70 is sufficiently large to accommodate the two tubes 60 and 61 in a press-fit or sealed engagement.

A guide tube 75 is engaged within the bore 71 at the opposite end 77 of the adaptor tube 70. The guide tube 75 includes a suction bore 78 therethrough. The guide tube 75 comprises a short section of relatively smaller diameter tube that provides a means for quick engagement to the suction hose of a saliva ejector device. The end of the suction hose is fed over the guide tube 75 until the end of the hose contacts the larger adaptor tube 70. It is understood that the guide tube 75 is only slidably received within the suction hose to permit quick and easy intermittent engagement with the suction source. However, the diameter of the guide tube 75 is sufficiently large to provide for efficient suction through the adaptor tube 70 and the suction tubes 60 and 61.

The tube arrangement of the embodiment shown in FIG. 6 provides the same beneficial features of the previous embodiments. In particular, the suction tube arrangement provides means for intermittent mating with a suction source in combination with the use of absorbent rolls supported by a conventional dental device. The suction tube arrangement of tubes 60, 61, 70, 75 and slide adaptor 65 can be readily configured for use with a variety of dental instruments, although the arrangement is shown in FIG. 6 with a Garmers type device. Moreover, each of the tubes are generally inexpensive so that they can be economically disposed of after each use. The slide collar 65 can be reused after sterilization since it is less likely to contact fluids in the patient's mouth.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A suction adapter for use with a dental instrument having a pair of roll-retaining members for supporting a number of absorbent rolls and a frame for supporting the roll-retaining members within the mouth of a patient, each absorbent roll having a central bore therethrough for engagement with a suction tube, the suction adapter comprising:

a body having a suction face and an attachment face;

engagement means in said body for removably engaging the frame of the dental instrument between the pair of roll-retaining members with said suction face oriented toward the mouth of the patient, whereby said body is supported by the frame when the dental instrument is in use and removable therefrom when the instrument is not in use;

a number of passages extending through said body, one end of each of said number of passages opening in a suction orifice at said suction face of said body, wherein said suction orifice of said number of passages is exposed for fluid connection to a suction source; and means at another end of each of said number of passages for sealingly engaging a suction tube.

2. The suction adapter of claim 1, wherein said engagement means includes an outwardly opening slot defined in said body at one of said attachment face or said suction face.

3. The suction adapter of claim 1, wherein said means for sealingly engaging a suction tube includes a tube attachment bore defined in each of said number of passages and opening at said attachment face, said tube attachment bore having a diameter large enough to receive an end of the suction tube therein.

4. The suction adapter of claim 1, wherein said body is formed of a plastic.

5. A combination comprising:

a number of absorbent rolls, each having a central bore therethrough;

an absorbent roll holder having means for removably retaining said number of absorbent rolls and a frame for supporting said number of rolls within the mouth of a patient;

a number of suction tubes, each of said number of suction tubes having a lumen extending therethrough and a number of apertures at one end communicating with said lumen, said one end being engagable within said central bore of a corresponding one of said number of absorbent rolls to support said one end when said corresponding one of said number of absorbent rolls is retained by said absorbent roll holder; and means at the opposite end of said number of suction tubes for providing intermittent connection of said number of suction tubes to a suction source, wherein said means for providing intermittent connection includes a suction adapter including:

a body;

engagement means in said body for removably engaging said frame of said roll holder to support said body thereon;

a number of passages defined through said body, one end of said number of passages opening in a suction orifice exposed at one face of aid body for fluid connection to a suction source; and means at another end of said number of passages for sealingly engaging a corresponding one of said number of suction tubes at another face of said body.

6. The combination of claim 5, wherein said engagement means includes an outwardly opening slot defined in said body.

7. The combination of claim 5, wherein said means for sealingly engaging one of said suction tubes includes a tube attachment bore defined in each of said number of passages and opening at said another face, said tube attachment bore having a diameter large enough to receive an end of one of said suction tubes therein.

8. The combination of claim 5, wherein said body is formed of a plastic material.

9. A combination comprising:
   a number of absorbent rolls, each having a central bore therethrough;
   an absorbent roll holder having means for removably retaining said number of absorbent rolls and a frame for supporting said number of rolls within the mouth of a patient;
   a number of suction tubes, each of said number of suction tubes having a lumen extending therethrough and a number of apertures at one end communicating with said lumen, said one end being engagable within said central bore of a corresponding one of said number of absorbent rolls to support said one end when said corresponding one of said number of absorbent rolls is retained by said absorbent roll holder; and
   means at an opposite end of said number of suction tubes for providing intermittent connection of said number of suction tubes to a suction source,
   wherein said absorbent roll holder is a Garmers device.

10. The combination of claim 9, wherein:
    said combination includes a plurality of absorbent rolls and a corresponding plurality of suction tubes; and
    said means for providing intermittent connection includes a suction adapter tube having a central lumen therethrough and a first end adapted to abuttingly engage the suction source for the application of suction through said central lumen,
    wherein said opposite end of each of said plurality of suction tubes is engaged within said central lumen at an opposite second end of said suction adaptor tube.

11. The combination of claim 10, further comprising means slidably disposed about each of said plurality of suction tubes for drawing each of said plurality of suction tubes into immediate adjacent relationship at adjustable locations along the lengths of said plurality of suction tubes.

12. The combination of claim 10, wherein said means for providing intermittent connection further includes a hollow guide tube engaged within said central lumen at said first end of said suction adaptor tube, said guide tube being sized to be slidably received within a suction hose of the suction source to guide the suction hose into abutting engagement with said first end of said suction adaptor tube.

13. A combination comprising:
    a plurality of absorbent rolls, each having a central bore therethrough;
    an absorbent roll holder having means for removably retaining said plurality of absorbent rolls and a frame for supporting said plurality of rolls within the mouth of a patient;
    a plurality of suction tubes, each of said plurality of suction tubes having a lumen extending therethrough and a number of apertures at one end communicating with said lumen, said one end being engagable within said central bore of a corresponding one of said plurality of absorbent rolls to support said one end when said corresponding one of said plurality of absorbent rolls is retained by said absorbent roll holder; and
    means at an opposite end of said plurality of suction tubes for providing intermittent connection of said plurality of suction tubes to a suction source,
    wherein said absorbent roll holder is a Garmers device having a buccal roll retaining member, a lingual roll retaining member and a bar interconnecting said roll retaining members;
    one of said plurality of suction tubes is engaged in an absorbent roll supported by said buccal roll retaining member; and
    another of said plurality of suction tubes is engaged in an absorbent roll supported by said lingual roll retaining member;
    said one and said another of said plurality of suction tubes passing on opposite sides of said bar of said Garmers device.

* * * * *